(12) United States Patent
El-Zehiry et al.

(10) Patent No.: US 10,671,833 B2
(45) Date of Patent: *Jun. 2, 2020

(54) ANALYZING DIGITAL HOLOGRAPHIC MICROSCOPY DATA FOR HEMATOLOGY APPLICATIONS

(71) Applicant: Siemens Healthcare Diagnostics Inc., Tarrytown, NY (US)

(72) Inventors: Noha El-Zehiry, Plainsboro, NJ (US); Shanhui Sun, Princeton, NJ (US); Bogdan Georgescu, Plainsboro, NJ (US); Lance Ladic, Robbinsville, NJ (US); Ali Kamen, Skillman, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/193,587

(22) Filed: Nov. 16, 2018

(65) Prior Publication Data

US 2019/0087638 A1 Mar. 21, 2019

Related U.S. Application Data

(63) Continuation of application No. 15/318,831, filed as application No. PCT/US2015/035945 on Jun. 16, 2015, now Pat. No. 10,176,363.

(Continued)

(51) Int. Cl.
*G06K 9/00* (2006.01)
*G03H 1/04* (2006.01)
(Continued)

(52) U.S. Cl.
CPC ..... *G06K 9/00147* (2013.01); *G01N 15/1463* (2013.01); *G01N 33/49* (2013.01);
(Continued)

(58) Field of Classification Search
CPC .................................................. G06K 9/00127
See application file for complete search history.

(56) References Cited

U.S. PATENT DOCUMENTS

| 4,125,828 A | 11/1978 | Resnick et al. |
| 6,330,350 B1 * | 12/2001 | Ahn .................... G01N 15/1475 382/134 |

(Continued)

FOREIGN PATENT DOCUMENTS

| CN | 102278951 A | 12/2011 |
| CN | 102812404 A | 12/2012 |

(Continued)

OTHER PUBLICATIONS

Gooddfellow, Ian J.; et al. (2014). "Generative Adversarial Networks". arXiv:1406.2661.
Zhu, Jun-Yan, Unpaired Image-to-Image Translation using Cycle-Consistent Adversarial Networks, ICCV 2017.
G. E. Hinton et al. Reducing the dimensionality of data with neural networks. Science, 313(5786):504-507, 2006. 4.

(Continued)

*Primary Examiner* — Nay A Maung
*Assistant Examiner* — Jose M Torres

(57) ABSTRACT

A method for analyzing digital holographic microscopy (DHM) data for hematology applications includes receiving a plurality of DHM images acquired using a digital holographic microscopy system. One or more connected components are identified in each of the plurality of DHM images and one or more training white blood cell images are generated from the one or more connected components. A classifier is trained to identify a plurality of white blood cell types using the one or more training white blood cell images. The classifier may be applied to a new white blood cell image to determine a plurality of probability values, each respective probability value corresponding to one of the plurality of white blood cell types. The new white blood cell image and the plurality of probability values may then be presented in a graphical user interface.

18 Claims, 15 Drawing Sheets

Related U.S. Application Data

(60) Provisional application No. 62/012,636, filed on Jun. 16, 2014.

(51) Int. Cl.

| | | |
|---|---|---|
| *G06K 9/62* | (2006.01) | |
| *G01N 15/14* | (2006.01) | |
| *G06T 7/136* | (2017.01) | |
| *G01N 33/49* | (2006.01) | |
| *G06K 9/46* | (2006.01) | |
| *G06T 7/00* | (2017.01) | |
| *G01N 15/00* | (2006.01) | |
| *G01N 15/10* | (2006.01) | |
| *G03H 1/00* | (2006.01) | |

(52) U.S. Cl.
CPC ....... *G03H 1/0443* (2013.01); *G06K 9/00127* (2013.01); *G06K 9/4604* (2013.01); *G06K 9/6268* (2013.01); *G06K 9/6269* (2013.01); *G06T 7/0012* (2013.01); *G06T 7/136* (2017.01); *G01N 2015/008* (2013.01); *G01N 2015/1006* (2013.01); *G03H 2001/005* (2013.01); *G06T 2207/30104* (2013.01)

(56) References Cited

U.S. PATENT DOCUMENTS

| | | | |
|---|---|---|---|
| 8,937,756 B2 | 1/2015 | Sebesta et al. | |
| 9,495,742 B2 | 11/2016 | Lagae et al. | |
| 9,668,699 B2 | 6/2017 | Georgescu et al. | |
| 10,176,363 B2* | 1/2019 | El-Zehiry | G01N 15/1463 |
| 2010/0002929 A1* | 1/2010 | Sammak | G06K 9/00127 382/133 |
| 2010/0169811 A1* | 7/2010 | Yamada | G01N 15/1475 715/764 |
| 2011/0074944 A1* | 3/2011 | Can | G01N 21/6458 348/79 |
| 2012/0034647 A1* | 2/2012 | Herzog | G01N 15/1475 435/34 |
| 2012/0147002 A1 | 6/2012 | Young et al. | |
| 2013/0046793 A1* | 2/2013 | Reznik | G06K 9/6261 707/797 |
| 2013/0094750 A1* | 4/2013 | Tasdizen | G06K 9/0014 382/134 |
| 2014/0056505 A1 | 2/2014 | Hoyt | |
| 2014/0139625 A1 | 5/2014 | Mathuis et al. | |
| 2014/0235956 A1* | 8/2014 | Kalkstein | G16H 50/20 600/300 |
| 2014/0270456 A1 | 9/2014 | Khare et al. | |
| 2014/0365161 A1* | 12/2014 | Naidoo | G01N 15/0227 702/127 |
| 2015/0049943 A1* | 2/2015 | Hamsici | G06K 9/4609 382/170 |
| 2015/0238148 A1 | 8/2015 | Georgescu et al. | |
| 2017/0091528 A1* | 3/2017 | Savvides | G06K 9/0014 |

FOREIGN PATENT DOCUMENTS

| | | |
|---|---|---|
| EP | 1701150 A1 | 9/2006 |
| EP | 2083268 A1 | 7/2009 |
| JP | 2015500475 A | 1/2015 |
| WO | WO2012112114 A1 | 8/2012 |
| WO | WO2013040345 A1 | 3/2013 |
| WO | WO2013080163 A1 | 6/2013 |
| WO | WO2013164823 A1 | 11/2013 |
| WO | WO2015195609 | 12/2015 |
| WO | WO2017050861 | 3/2017 |
| WO | WO2017157555 | 9/2017 |

OTHER PUBLICATIONS

Parthasarathy, D.; "Classifying White Blood Cells With Deep Learning (Code and data included!)"; 2017; blog; https://blog.athelas.com/classifying-white-blood-cells-with-convolutional-neural-networks-2ca6da239331.

European Search Report dated Jul. 4, 2018 in corresponding European patent application No. 18159357.5.

Diaz, Gloria, et al., "automatic analysis of microscopic images in hermatological cytology applications", Dec. 31, 2009, pp. 1-26.

Sharif, J.M., et al., "red blood cell segmentation using masking and watershed algorithm: a preliminary study", biomedical engineering (ICOBE), 2012, international conference on IEEE, Feb. 27, 2012, pp. 258-262.

Baghli Ismahan et al: "Hybrid framework based on Evidence theory for blood cell image"; Proceedings of SPIE —The International Society for Optical Engineering, Feb. 2014; pp. 1 to 8; Abstract.

J O Ricardo et al: "Digital holography microscopy in 3D biologic samples analysis", Journal of Physics: Conference Series, vol. 274, Jan. 1, 2011 (Jan. 1, 2011), p. 012066.

Japanese Office Action dated Feb. 20, 2018 in corresponding Japanese Application No. 2016-572573.

Guan-cai Han:"Mode Analysis of Several Typical Blood Cells under Optical Phase Models by Virtullab Technique"; The 1st International Conference on Information Science and Engineering (ICISE2009); 2009; pp. 3677 to 3680, p. 3677, p. 3980 left column.

El-Zehiry, Noha, et al; "Combinatorial optimization of the piecewise constant Mumford-Shah functional with application to scalar/vector valued and volumetric image segmentation." Image and Vision Computing 29.6 (2011 ): 365-381.

Evans, Evan, and Yuan-Cheng Fung. "Improved measurements of the erythrocyte geometry-" Microvascular research 4.4 (1972): 335-347.

D.G. Lowe. Object recognition from local scale-invariant features. In: Proc. ICCV 1999, Kerkyra, Greece, pp. 1150-1157.

C.-W. Hsu and C.-J. Lin. A comparison on methods for multi-class support vector machines, IEEE Transactions on Neural Networks, 13 (2002), 415-425.

M. Varma and A. Zisserman, (2002) Classifying images of materials: Achieving viewpoint and illumination independence, in ECCV (3), 2002, pp. 255-271.

D. Nister, H. Stewenius. Scalable Recognition with a Vocabulary Tree. In: Proc. CVPR 2006.

P. Khurd, C_ Bahlmann, P. Maday, A. Kamen, S_ Gibbs-Strauss, E. Genega, and J_ Frangioni, (2010)"Computer-aided Gleason grading of prostate cancer histopathologicalimages using texton forests," in Proc. IEEE Int. Symp. Biomed.Imaging, Apr. 2010, pp. 636-639.

Japanese Office Action dated Apr. 16, 2019 in corresponding Japanese Patent Application No. 2018-024140.

Moon, Inkyu, et al. "Automated statistical quantification of three-dimensional morphology and mean corpuscular hemoglobin of multiple red blood cells." Optics express 20.9 (2012): 10295-10309.

Chinese Office Action dated Jun. 26, 2019 in corresponding Chinese Patent Application No. 201810094733.4.

Pham Hoa V. et al; "Real Time Blood Testing Using Quantitative Phase Imaging"; PLOS ONE, vol. 8; Issue 2; Feb. 2013; pp. 1-9.

Rawat Jyoti et al; "Review of Leukocyte Classification Techniques for Microscopic Blood Image"; 2015 2nd International Conference on Computing for Sustainable Global Development (INDIACom), New Delhi; 2015; pp. 1948-1954.

Office Action dated Jan. 9, 2019 in corresponding Chinese Patent Application No. 201580032575.4.

Chinese Office Action dated Dec. 11, 2019 in corresponding Chinese Patent Application No. 201810094733.4.

Bi, Lei et al; "Modeling of light scattering by biconcave and deformed red blood cells with the invariant imbedding T-matrix method"; Journal of biomedical optics; vol. 18; No. 5; 2013.

* cited by examiner

| Cell Type | Nr. of Images | Nr. Cells | Training Cells | Testing Cells |
|---|---|---|---|---|
| Monocyte | 110 | 191 | 100 | 91 |
| Neutrophil | 117 | 155 | 100 | 55 |
| Basophil | 129 | 140 | 100 | 40 |
| T Cell | 110 | 406 | 100 | 306 |

*Fig. 8A*

| Classifier Type1-Type2 | | Correct Classification rate for Type 1 | Correct Classification rate for Type 2 | Average Correct Classification Rate |
|---|---|---|---|---|
| Monocyte | Neutrophil | 81.32% | 74.55% | 77.93% |
| Monocyte | Basophil | 89.01% | 100% | 94.51% |
| Monocyte | T Cell | 90.11% | 95.42% | 92.77% |
| Basophil | Neutrophil | 95% | 92.73% | 93.86% |
| Basophil | T Cell | 80% | 89.54% | 84.77% |
| Neutrophil | T Cell | 90.91% | 94.44% | 92.68% |
| Monocyte | Eosinophil | 84.62% | 82.42% | 83.52% |
| Neutrophil | Eosinophil | 80% | 68% | 74% |
| Basophil | Eosinophil | 100% | 96.7% | 98.35% |
| TCell | Eosinophil | 93.46% | 98.9% | 96.18% |

*Fig. 8B*

| Classifier Type1-Type2 | | Correct Classification rate for Type 1 | Correct Classification rate for Type 2 | Average Correct Classification Rate |
|---|---|---|---|---|
| Monocyte | Neutrophil | 84.6% | 70.9% | 79.4% |
| Monocyte | Basophil | 96.7% | 96.7% | 97.7% |
| Monocyte | T Cell | 92.3% | 96.7% | 95.7% |
| Basophil | Neutrophil | 100% | 96.3% | 97.8% |
| Basophil | T Cell | 97.5% | 91.8% | 92.5% |
| Neutrophil | T Cell | 94.54% | 95.7% | 95.5% |
| Monocyte | Eosinophil | 96.7% | 97.8% | 97.2% |
| Neutrophil | Eosinophil | 72.7% | 82.4% | 82.4% |
| Basophil | Eosinophil | 100% | 100% | 100% |
| TCell | Eosinophil | 91.8% | 97% | 92.5% |

*Fig. 12*

ANALYZING DIGITAL HOLOGRAPHIC MICROSCOPY DATA FOR HEMATOLOGY APPLICATIONS

CROSS REFERENCE TO RELATED APPLICATIONS

This application is a continuation of U.S. application Ser. No. 15/318,831 filed Dec. 14, 2016, which is a national phase filing under 35 U.S.C. § 371 of international patent application no. PCT/US2015/035945 filed Jun. 16, 2015, which claims the benefit of U.S. provisional application Ser. No. 62/012,636 filed Jun. 16, 2014, which is incorporated herein by reference in its entirety.

TECHNICAL FIELD

The present disclosure relates generally to analyzing digital holographic microscopy (DHM) for hematology applications. The various systems, methods, and apparatuses described herein may be applied to, for example, red blood cell (RBC) volume measurement and white blood cell (WBC) differential (cell type classification) applications.

BACKGROUND

Digital holographic microscopy (DHM), also known as interference phase microscopy, is an imaging technology that provides the ability to quantitatively track sub-nanometric optical thickness changes in transparent specimens. Unlike traditional digital microscopy, in which only intensity (amplitude) information about a specimen is captured, DHM captures both phase and intensity. The phase information, captured as a hologram, can be used to reconstruct extended morphological information (such as depth and surface characteristics) about the specimen using a computer algorithm. Modern DHM implementations offer several additional benefits, such as fast scanning/data acquisition speed, low noise, high resolution and the potential for label-free sample acquisition.

Conventional cellular analysis techniques such as volume measurement and classification rely on two-dimensional cellular images that lack topographical information. Thus, while these techniques may analyze a cell based on information such as intensity, their accuracy is limited due to a lack of knowledge of the size and shape of the cell. Accordingly, it is desired to provide cellular analysis techniques which are applicable to imaging modalities such as DHM that provide more detailed information regarding cellular structure.

SUMMARY

Embodiments of the present invention address and overcome one or more of the above shortcomings and drawbacks, by providing methods, systems, and apparatuses related to analyzing digital holographic microscopy (DHM) for hematology applications. Additionally, as explained in further detail in the disclosure, the technology described herein may be applied to other clinical applications as well.

The ability of DHM to achieve high-resolution, wide field imaging with extended depth and morphological information in a potentially label-free manner positions the technology for use in several clinical applications. For example, in the area of hematology DHM may be used for red blood cell (RBC) volume measurement, white blood cell (WBC) differential (cell type classification). For urine sediment analysis DHM allows for scanning a microfluidic sample in layers to reconstruct the sediment (possibly without waiting for sedimentation); improving the classification accuracy of sediment constituents. DHM may also be used for tissue pathology applications through utilization of extended morphology/contrast of DHM (e.g. to discriminate cancerous from healthy cells, in fresh tissue, without labeling). Similarly, for rare cell detection applications may utilize extended morphology/contrast of DHM (e.g. to differentiate rare cells such as circulating tumor/epithelial cells, stem cells, infected cells, etc.).

According one aspect of the present invention, as described in some embodiments, a method for analyzing digital holographic microscopy (DHM) data for hematology applications includes receiving DHM images acquired using a digital holographic microscopy system. One or more connected components are identified in each of the plurality of DHM images. One or more training white blood cell images are generated from the one or more connected components and a classifier is trained to identify white blood cell types using the one or more training white blood cell images. When a new DHM image is received, a new white blood cell image is extracted from the DHM image. Then classifier may then be applied to the new white blood cell image to determine probability values, with each respective probability value corresponding to one of the white blood cell types. The new white blood cell image and the plurality of probability values may then be presented in a graphical user interface. In some embodiments, a complete blood cell (CBC) test may be performed using the probability values.

Various enhancements, modifications, or additions may be made to the aforementioned in different embodiments of the present invention. For example, in some embodiments, prior to identifying the one or more connected components, a thresholding is applied to the each of the plurality of DHM images to highlight bright spots in each respective DHM image. Components having a size below a predetermined threshold value (i.e., small connected components) may then be removed. In some embodiments, the classifier is a K-Nearest Neighbor (K-NN) classifier. Such a classifier may use texton-based texture features extracted from each of the plurality of DHM images to classify the new DHM image. In other embodiments, the classifier is a visual vocabulary dictionary (e.g., vocabulary histogram) trained using hierarchical k-means and a scale-invariant feature transform (SIFT) descriptor as a local image feature. For example, dense SIFT descriptors may be extracted from each of the plurality of DHM images and used to construct a binary search tree representative of a vocabulary dictionary structure. The visual vocabulary dictionary can then be generated based on the binary search tree. A one against one n-label supporting vector machine (SVM) may be used for identifying one or more of the plurality of white blood cell types in the DHM images. In still other embodiments, the classifier is a deep learning classifier trained using an auto-encoder convolutional neural network (CNN).

Additionally, in some embodiments of the aforementioned method, a digital staining technique is applied to the white blood cell images. For example, in one embodiment, a mapping is determined between optical density and coloring associated with a staining protocol. Optical density information associated with the new white blood cell image is also determined. Prior to presenting the new white blood cell image, the new white blood cell image is colorized using the mapping and the optical density information.

According to another aspect of the present invention, as described in some embodiments, an article of manufacture for analyzing digital holographic microscopy (DHM) data for hematology applications comprise a non-transitory, tangible computer-readable medium holding computer-executable instructions for performing the aforementioned method. This article of manufacture may further include instructions for any of the additional features discussed above with respect to the aforementioned method.

In other embodiments of the present invention, a system for analyzing digital holographic microscopy (DHM) data for hematology applications comprises a networking component, a modeling processor, and a graphical user interface. The networking component is configured to communicate with a digital holographic microscopy system to retrieve training DHM images and a test DHM image. The modeling processor is configured to: identify one or more connected components in each of the training DHM images, generate one or more training white blood cell images from the one or more connected components, and train a classifier to identify white blood cell types using the one or more training white blood cell images. The modeling processor is further configured to extract a test white blood cell image from the test DHM image, and apply the classifier to the test white blood cell image to determine probability values, with each respective probability value corresponding to one of the white blood cell types. The graphical user interface is configured to present the test white blood cell image and the probability values.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIG. 8A provides a table showing an example of a data set that may be used for training and testing for each cell type, as may be used in some embodiments;

FIG. 8B shows pairwise classification results obtained using texton features and KNN classifier for this sample case, as may be obtained according to some embodiments;

FIG. 12 shows Pairwise Classification results using SIFT and SVM classification, obtained according to some embodiments;

DETAILED DESCRIPTION

The following disclosure describes the present invention according to several embodiments directed at methods, systems, and apparatuses related to analyzing digital holographic microscopy (DHM) for hematology and other clinical applications. Briefly, the techniques discussed herein comprise of three principle ideas that may be applied in different configurations in the various embodiments described herein. First, in some embodiments, red blood cell (RBC) volume estimation is performed using parametric modeling of erythrocytes to regularize the raw DHM data to match physical models of the erythrocytes, in an attempt to eliminate any distortion caused during the image acquisition process. Second, in some embodiments, label-free differentiation of white blood cells (WBCs) captured by DHM is performed using a machine learning algorithm which extract characteristic topological changes from a set of training samples DHM images for each sub-type of WBCs (namely, monocytes, neutrophils, basophils, lymphocytes, eosinophils). The machine learning algorithm then classifies a new cell into one of the categories automatically based on the learnt DHM image based features. Third, in some embodiments, "digital staining" or "pseudo-coloring" of the classified DHM images of the cells is performed to resemble conventional staining techniques. The digital staining method described herein uses a matched pair of DHM and stained images of a set of cells, and a regression function is learnt to map the DHM image pixel (representing the topology of the cell constituents to a RGB color scheme of conventional staining techniques).

Figure 1:
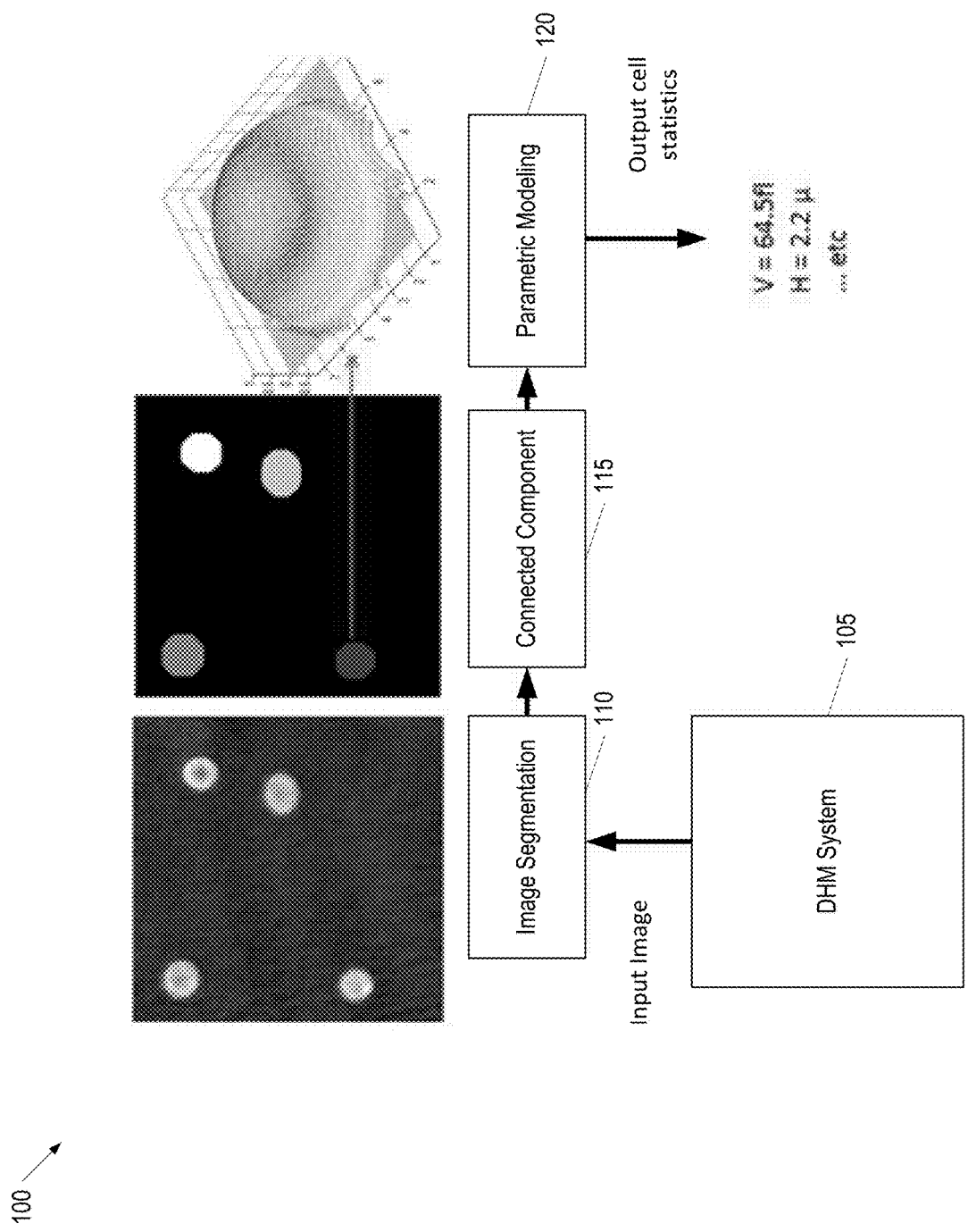
FIG. 1 provides an illustration of a framework for processing DHM images for erythrocyte volume computation, according to some embodiments.

FIG. 1 provides an illustration of a framework 100 for processing DHM images for erythrocyte volume computation, according to some embodiments. Briefly, a DHM System 105 is used to acquire one or more input images. The Digital Holographic Microscopy System 105 may be any system known in the art capable of acquiring DHM images. An Image Segmentation Component 110 performs segmentation of the erythrocytes in the acquired input images. Next, a Parametric Modeling Component 115 develops a model of the erythrocytes (e.g., using Cassini ovals). Then, a Parametric Modeling Component 120 calculates thickness information of each erythrocyte which, in turn, can be used to determine the erythrocyte's volume.

Various segmentation techniques may be applied to the input image to segment the erythrocytes. For example, in some embodiments, the segmentation problem performed by the Image Segmentation Component 110 is formulated as an energy minimization problem that minimizes the piecewise constant Mumford-Shah energy functional in a combinatorial optimization framework. The segmentation energy can be described as follows. Given an image u and an image of interest u: $\Omega \rightarrow R$, where $\Omega$ is an open bounded subset in R2 that comprises several connected components $\Omega_i$ and bounded by a closed boundary $C=\partial\Omega$, find a piecewise constant approximation such that u is constant within the components $\Omega_i$ and sharp in the transition across the boundary C. This is formulated as:

$$F(x1, x2, \ldots, xn) = \mu \Sigma_{epq \in E} w_{pq} |x_p - x_q| + \Sigma_p |u(p) - c_1|^2 x_p + \Sigma_p |u(p) - c_1|^2 (1 - x_p) \quad (1)$$

where $x_p$ is a binary variable that indicates whether a particular pixel p=(x, y) belongs to the cell or to the background. A binary variable $x_p$ for each pixel p=(x, y)$\in \Omega$ is set such that $$x_p = \begin{cases} 1 & \text{if } p \in U_i \Omega_i \\ 0, & \text{otherwise} \end{cases} \quad (2)$$

The constants $c_1$ and $c_2$ represent the piecewise constant approximation of the input DHM image, $w_{pq}$ represents the weights of the Euclidean length regularization, and $\mu$ is a weighting coefficient that defines the contribution of the length regularization to the segmentation energy. A relatively high value for mu may be used to avoid separating the nucleus from the rest of the cell.

Figure 2:
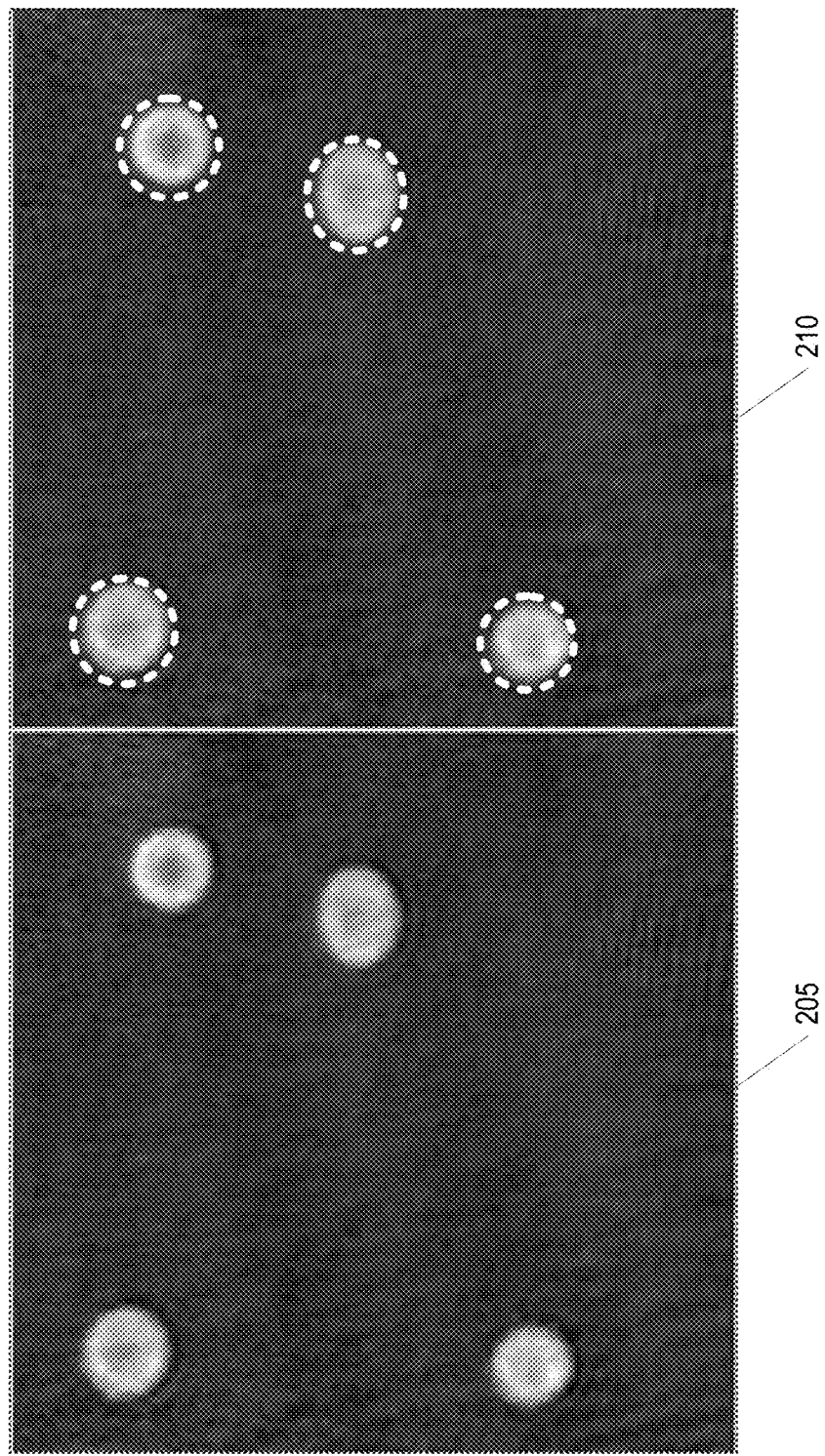
FIG. 2 provides an example illustration of segmentation of erythrocytes in optical path difference DHM (OPD-DHM) images, as may be performed in some embodiments.

FIG. 2 provides an example illustration of Segmentation of erythrocytes in optical path difference DHM (OPD-DHM) images. Image 205 shows the input image, while image 210 shows the delineation (represented by a dotted line) of the erythrocyte boundaries is imposed on the image 205.

Figure 3:
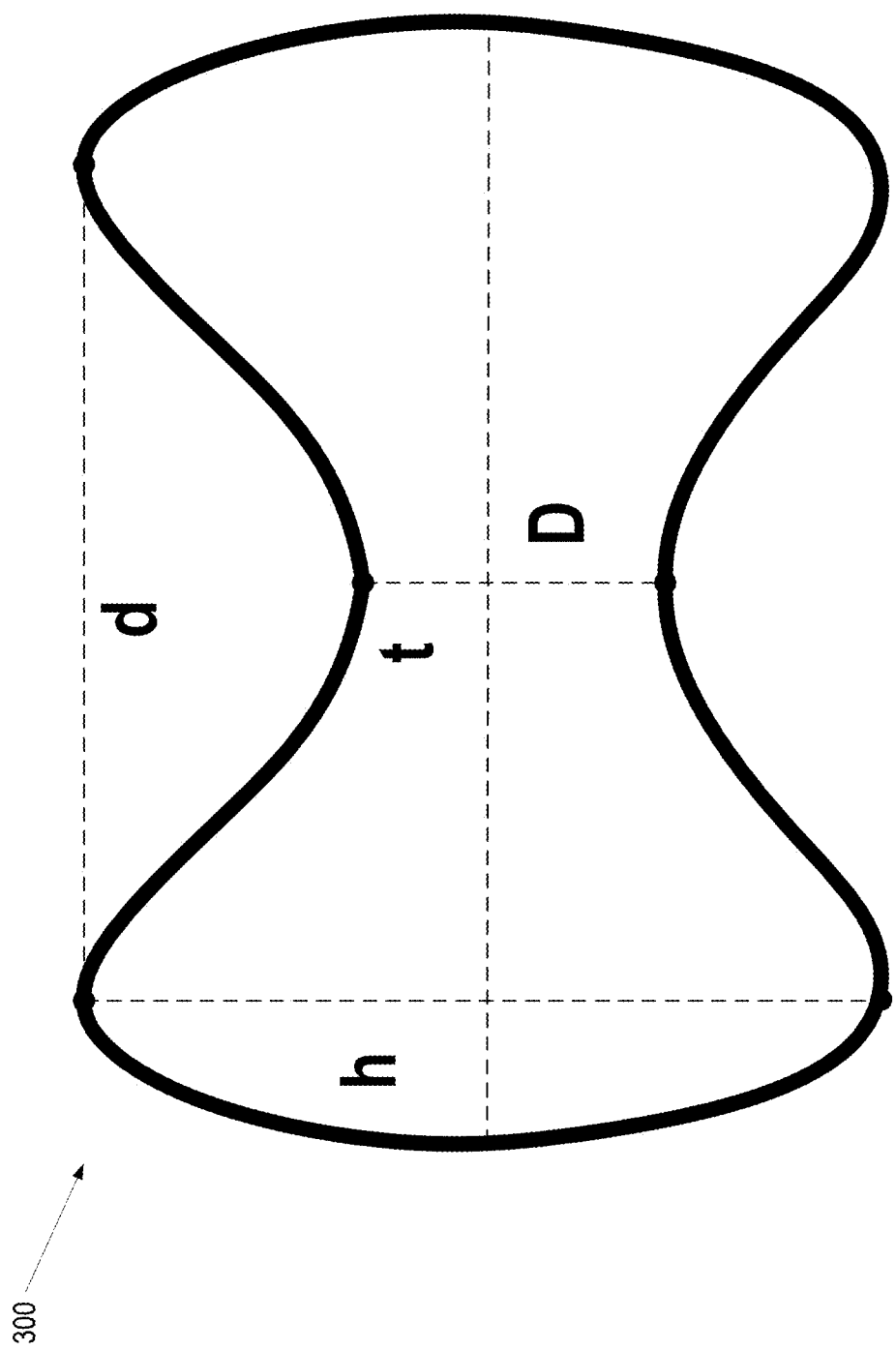
FIG. 3 shows a geometry model of a normal erythrocyte, as may be utilized in some embodiments.

A normal erythrocyte is generally shaped as a biconcave disk to achieve a large surface area-to-volume ratio. For example, FIG. 3 shows a geometry model 300 of a normal erythrocyte. There are four main parameters that affect the shape of the cell (shown in FIG. 3): the diameter of the cell (D), the minimum dimple thickness (t), the maximum thickness (h) and the diameter of the circle that determines the maximum thickness (d).

Using the geometric understanding presented in FIG. 3, there are several bi-concave models for the erythrocyte surface representation that may be applied by Parametric Modeling Component 120 to characterize the shape and geometry of each erythrocyte. For example, some embodiments utilize the Evans-Fung Model technique generally known in the art which utilizes the following equation:

$$z(\rho) = \pm \sqrt{1 - \left(\frac{\rho}{R}\right)^2} \left[ c0 + c1\left(\frac{\rho}{R}\right)^2 + c2\left(\frac{\rho}{R}\right)^4 \right] \quad (3)$$

where R is the radius of the cell (R=D/2) and p is the horizontal distance from the center of the cell. To estimate the model parameters c0, c1 and c2 we minimize the sum squared error between the depth map as estimated from the parametric model and the depth observed from the DHM. The sum squared error of the thickness profile is expressed as:

$$SSE_{thickness} = \sum_p \left( z(\rho) - \frac{u(\rho)}{2} \right)^2 \quad (4)$$

Figure 4:
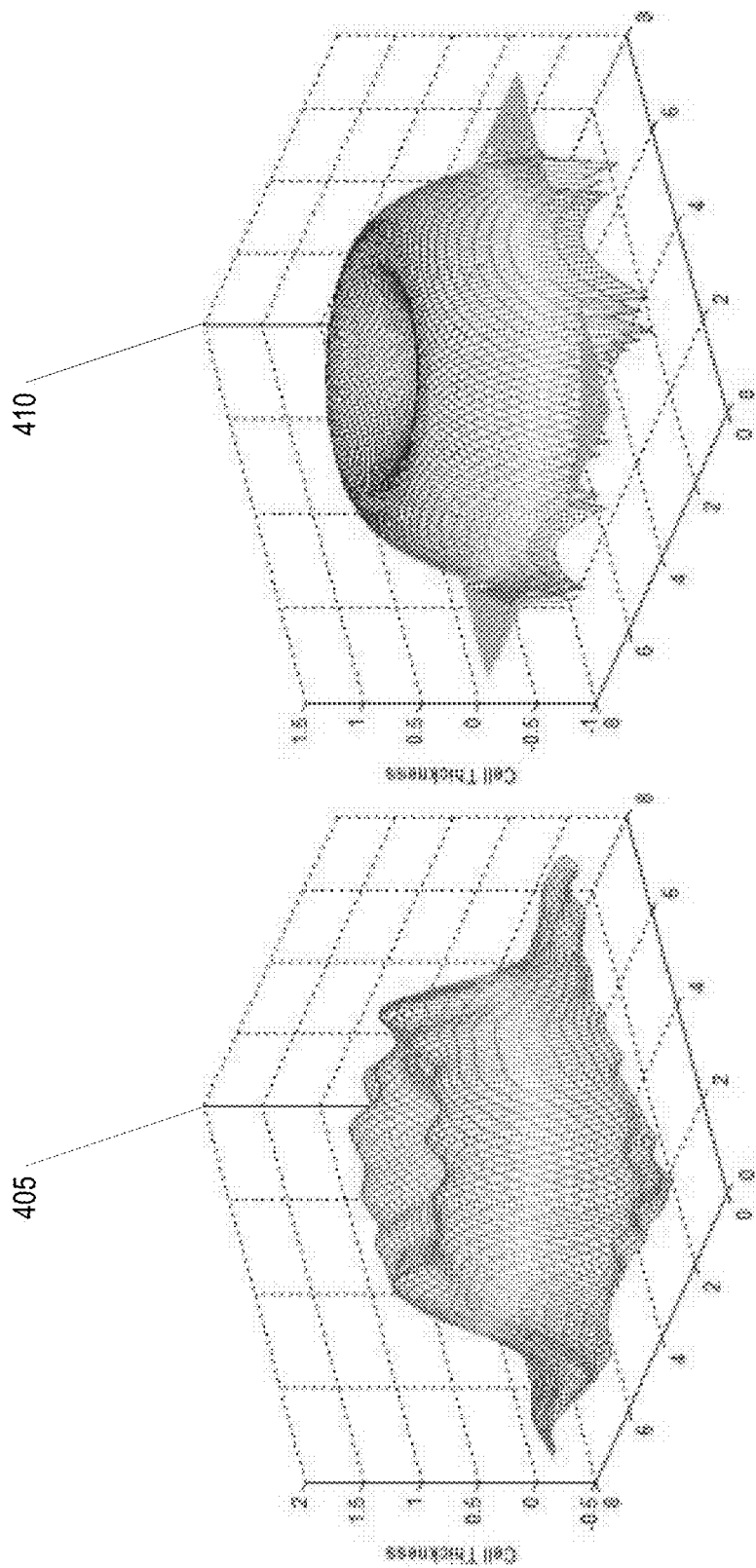
FIG. 4 provides an example of the parametric modeling of the erythrocytes which illustrates the regularization.

In some embodiments, the parametric modeling of the cell regularizes the cell surface to match the physical models of the erythrocytes and eliminate any distortion caused during the image acquisition process. FIG. 4 provides an example of the parametric modeling of the erythrocytes which illustrates the regularization. In Image 405, the cell surface is depicted as observed from the DHM image. Image 410 shows the cell surface as characterized by the Evans-Fung model.

After performing the segmentation and the parametric modeling for each cell, the volume of each RBC may be computed. The RBC volume may then be used as a clinical measurement in and of itself, or it may be used to derive additional clinically significant values. For example, the calculation of RBC volume may be used in determining mean cell volume (MCV) which, in turn, is a critical parameter in a complete blood count (CBC).

Figure 5:
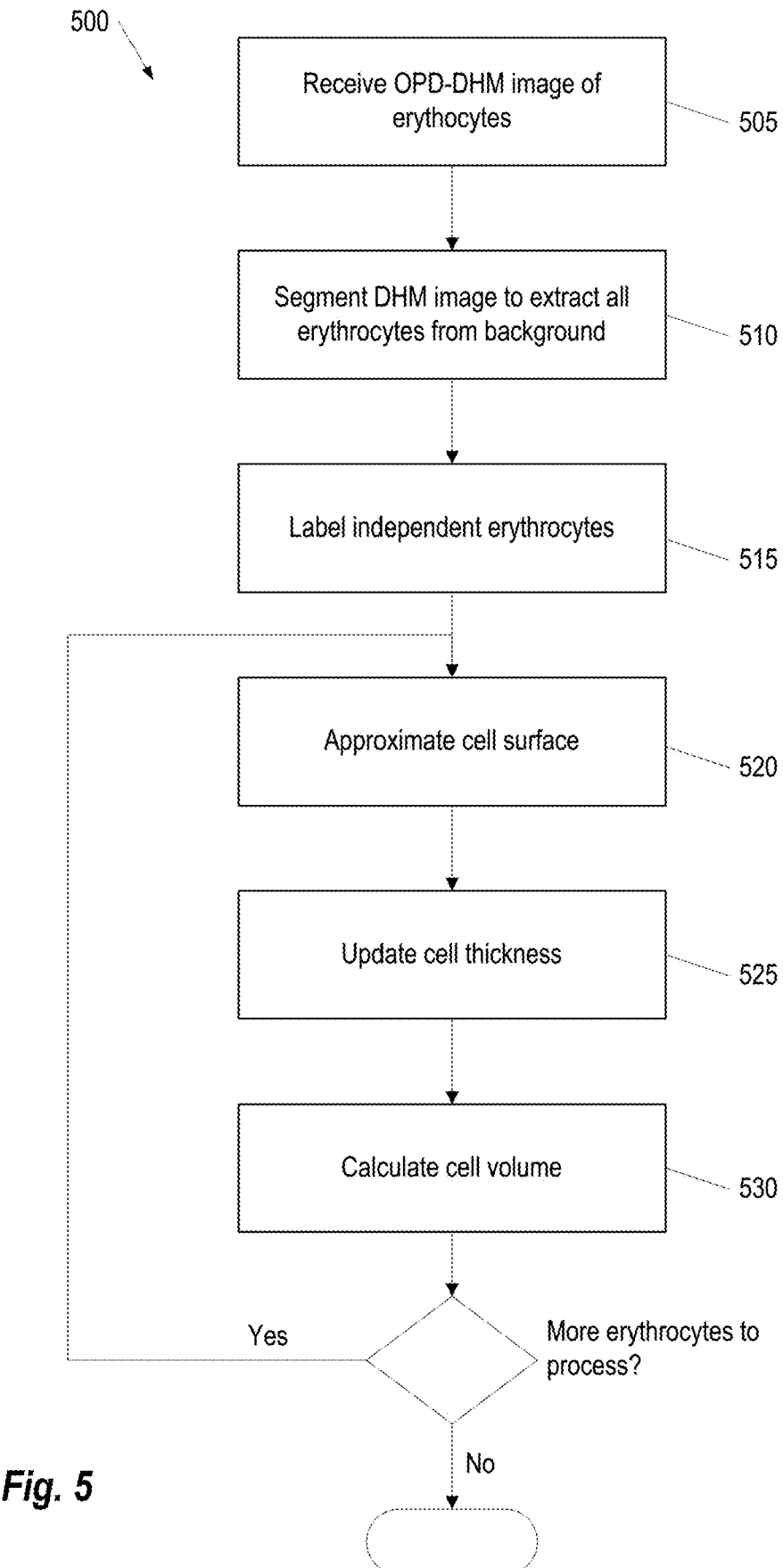
FIG. 5 provides an illustration of a process for calculating cell volume, according to some embodiments.

FIG. 5 provides an illustration of a process 500 for calculating cell volume, according to some embodiments. At step 505, an OPD-DHM image of erythrocytes is received. Next, at step 510, the DHM image is segmented to extract all the erythrocytes from the background. Segmentation may be performed, for example, using the combinatorial piecewise constant Mumford-Shah energy functional or any similar technique generally known in art. At step 515, connected component analysis is applied to the segmentation mask to label the independent erythrocytes.

Continuing with references to FIG. 5, at steps 520-530 a measurement process is performed for each erythrocyte. At step 520, the cell surface is approximated, for example, using the Evans-Fung technique. The sum squared differences in Equation 4 are optimized and the model parameters C0, C1 and C2 are computed. Next, at step 525, the model is used to estimate the updated cell thickness z(p) using Equation 3. Then, at step 530, the updated cell thickness is used to calculate the cell volume. The output of the process 500 is a volume for each erythrocyte.

The process 500 can be extended to provide the mean hemoglobin content of the cell as well. For this, a conventional hematology analyzer may be used for calibration of mean cell volume and conversion of optical density map based volume to the average hemoglobin content.

Differential blood tests measure the percentage of each type of white blood cell type in a blood cell sample. Identifying each type of white blood cell is a crucial preliminary step to blood differential analysis that is used to diagnose diseases such as infections, anemia and Leukemia. To address this step, the system described herein may be applied to differentiate among the different white blood cell types. Specifically, the described system aims to differentiate five different types of white blood cells, namely: monocytes, basophils, neutrophils, eosinophils and lymphocytes. Briefly, a pipeline of processing the white blood cells comprises the following three steps. The first step is pre-processing where various types of white blood cells are identified and isolated. The second step is training where a classifier is trained from the extracted cells. The third step is classification where a classifier is used to categorize unseen cells. Each of these steps will now be discussed in detail.

Figure 6:
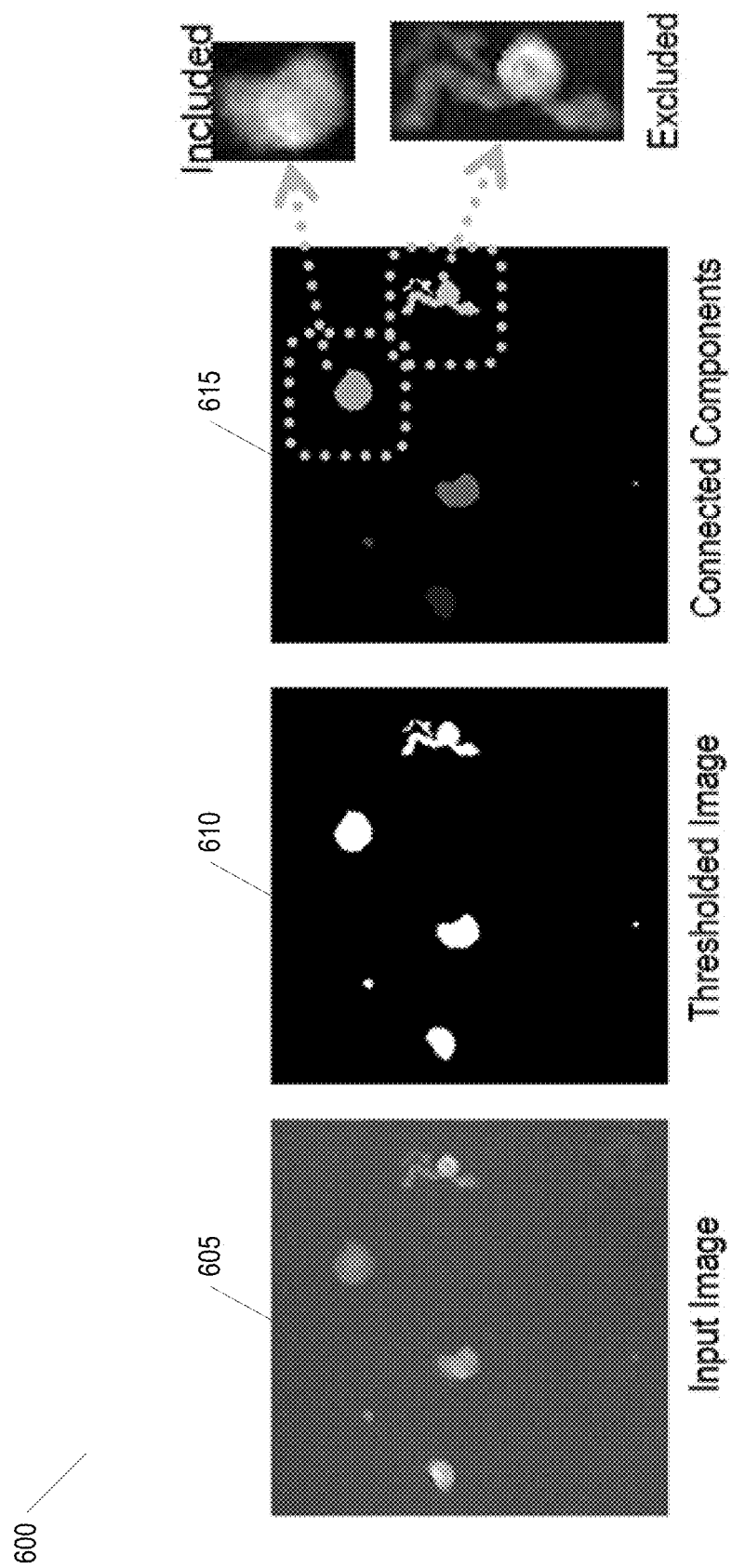
FIG. 6 provides an illustration of a pre-processing framework for classifying white blood cells, as it may be applied in some embodiments.

FIG. 6 provides an illustration of a pre-processing framework 600 for classifying white blood cells, as it may be applied in some embodiments. During the pre-processing step, a pipeline is used to prepare the training patches for the classifier training step. Initially, a threshold is applied to an input image 605 to capture the bright spots (that are highly likely to be cells). After thresholding, a connected component analysis is applied to the thresholded image 610. Then, as illustrated in image 615, the component size is calculated for each connected component. A component is rejected if its size is below or above predefined thresholds t1 and t2. The rejected components are excluded from training and testing. The patches (patch is a rectangular box including the connected component), including the remaining components are used to train the classifier (e.g., a K-Nearest Neighbor classifier).

Following the pre-processing framework 600, various machine learning algorithms may be used for performing five part differential on DHM images of white blood cells. For example, in some embodiments, a texton-based approach is used, where the textural characteristics of DHM image of cells are used as the main discriminating feature. In other embodiments, a more data driven approach is employed, where a dictionary of image patches is learned and used to represent the entire image as a histogram. The histogram is then used as the main feature for classification between various cell sub-types. In other embodiments, classification is based on a convolutional neural network with multiple layers to perform feature extraction, selection, and classification at once with a multi-layer network. Each of these different approaches is described in detail below.

Figure 7:
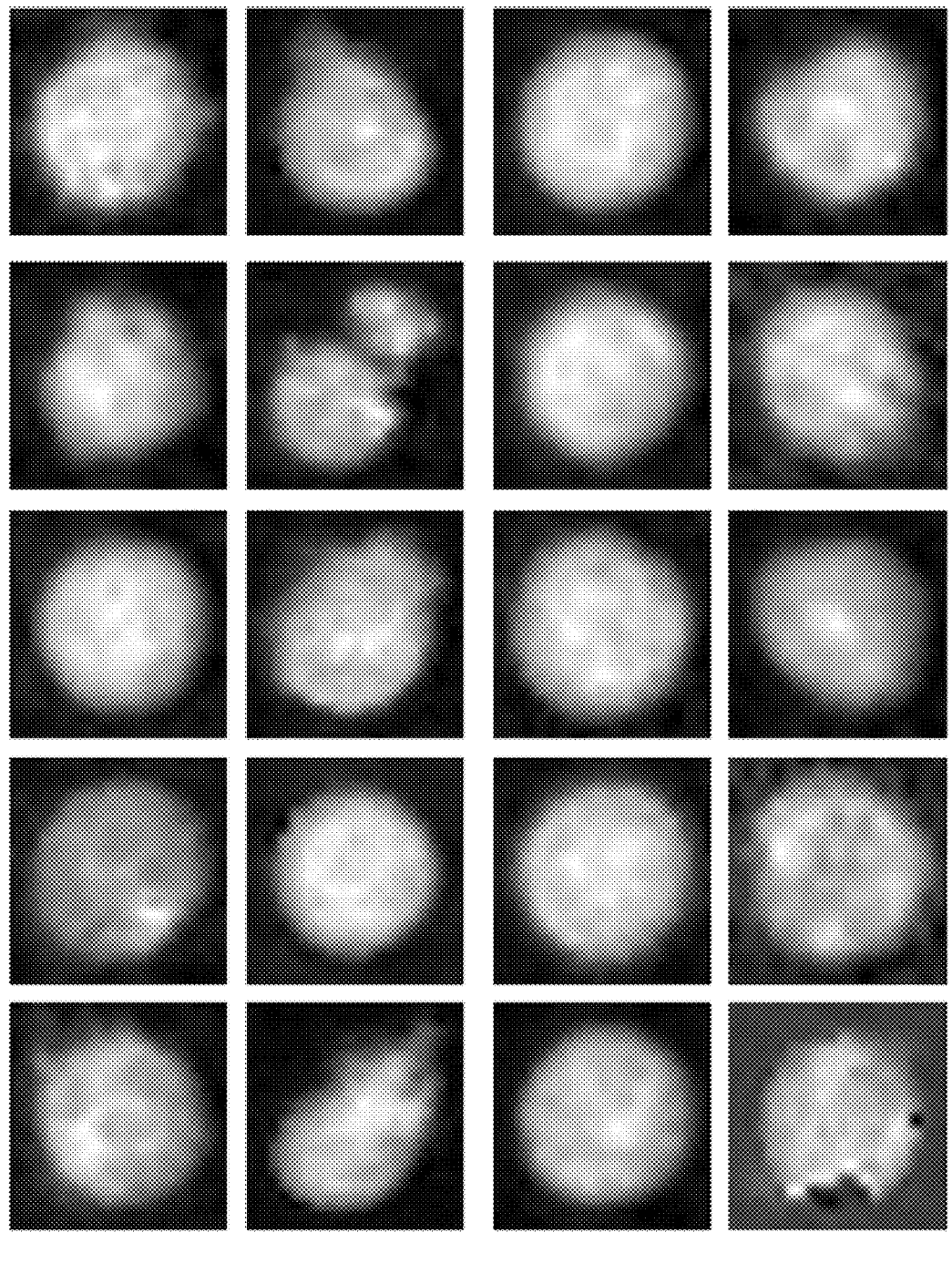
FIG. 7 shows a sample of the white blood cells used in training and testing, according to some embodiments.

As is generally understood in the art, image classification algorithms are trained using a data set of representative images. One example of a training data set is illustrated in FIG. 7. In this example, cell images are labelled in one of four categories: monocyte, basophil, neutrophil, and lymphocytes. It should be noted that this training set is but one example of a data that may be used in training the classifier. For example, other training sets employed in some embodiments may include additional categories (e.g., eosinophils). Additionally (or alternately), the categories could have a finer level of granularity.

In embodiments where the texton-based approach is used for classification, the extracted patches that include the preprocessed cell images are used to train a K-Nearest Neighbor (K-NN) classifier. The classifier utilized texton based texture features extracted from each patch. Textons are the representation of small texture features by a collection of filter bank responses. Texton based texture classifiers use the histograms of the textons to characterize the texture by the frequency of the textons in a particular patched as compared to the textons of the training data set. The texton features are used, in particular, because it is pathologically proven that the granularity of cell nuclei differ in the different cell types and this can be captured using texture features.

To illustrate the texton-based approach, consider a combination of the texton based texture feature representation with a simple K-NN classifier. FIG. 8A provides a table showing an example of a data set that may be used for training and testing for each cell type. The classification rate obtained for this example dataset in all the pairwise classifications varies from 75% to 95%. FIG. 8B shows pairwise classification results obtained using texton features and KNN classifier for this sample case.

To provide a multi-label classifier using the previous pairwise classification, one or more pairwise classifiers may be combined using voting. Ideally four classifiers should agree on the class label and 6 classifiers would provide random labeling. For example, if 10 classifiers are denoted as C1 to C10, the final class label L for an unknown sample S can be represented as the mode (most frequent value) of the labels of the 10 classifiers. In other words, the majority vote of the 10 pairwise classifiers is labeled for the multi-label classification problem. Combining all the pairwise classification to one multi-label classifier yielded a 76.5% correct classification rate for the example dataset set presented in FIG. 8A.

In some embodiments, a bag of visual words (BOW) approach may be used to solve this multi-class based image classification problem. In the BOW approach, the global image features are represented by vectors of occurrence counts of visual words (a histogram over a vocabulary dictionary based on local image feature). These global image features are then used for classification. The pipeline may be divided into three stages: offline vocabulary learning, image classification training and testing. In the offline vocabulary learning stage, a visual vocabulary dictionary may be trained using hierarchical k-means and SIFT (scale-invariant feature transform) descriptor as local image feature. For classification, one against one n-label supporting vector machine (SVM) may be utilized. To avoid an over-fitting problem, two approaches may be employed. First, each training image may be perturbed at random degree. Secondly, SVM parameters may be determined for the kernel using cross validation on the training data set.

Figure 9:
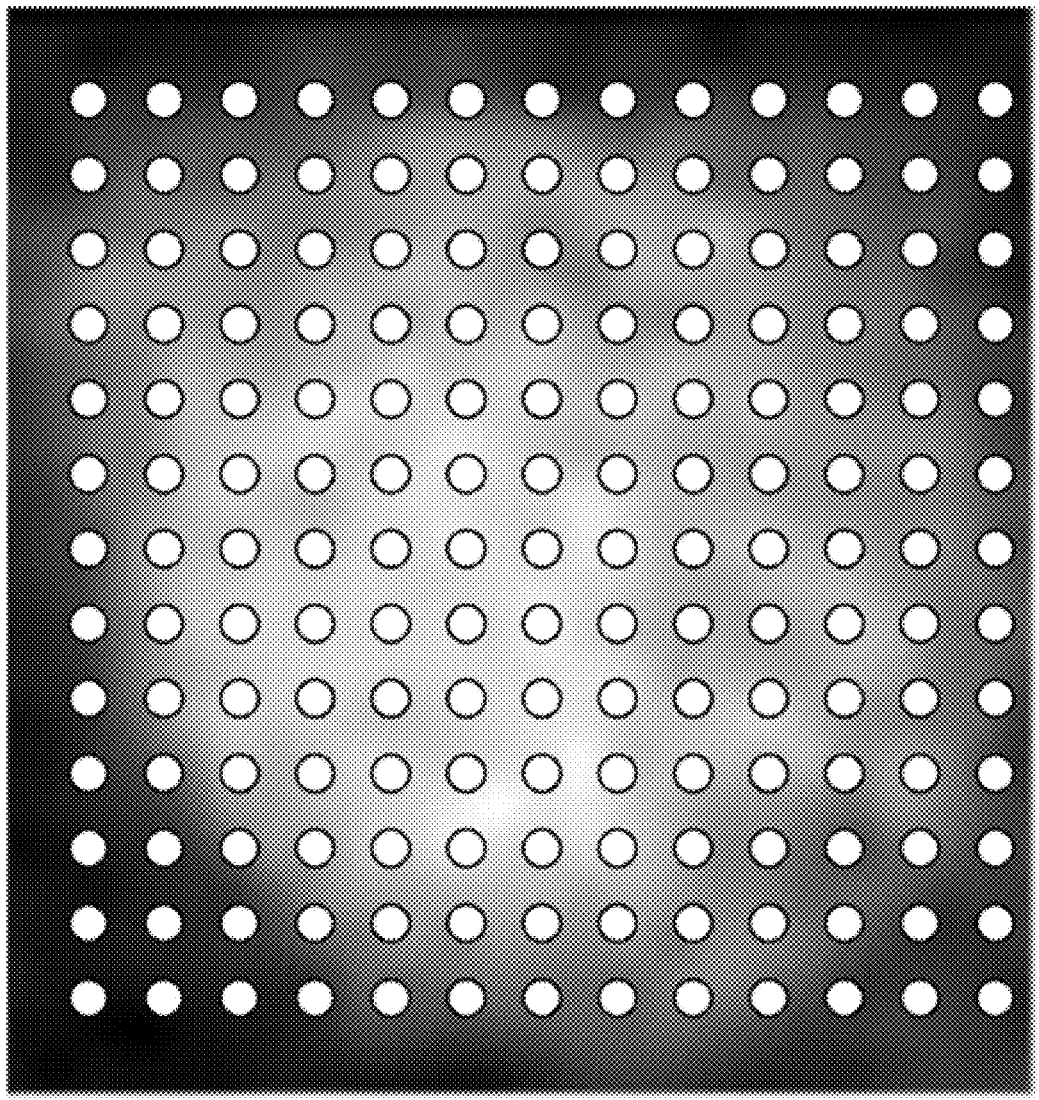
FIG. 9 provides an example of local image feature sampling, as it may be applied in some embodiments.

SIFT descriptor describes invariant local image structure and capturing local texture information. Dense SIFT descriptors may be computed for every $n_s$ pixels of each image (w×h, where w and h are image width and height respectively. For example, a 128 dimension SIFT descriptor may be used and, thus, there are about $(w/n_s) \times (h/n_s) \times 128$ local image features per image. FIG. 9 provides an example of local image feature sampling, as it may be applied in some embodiments. In this example, each white dot represents a location where 128 dimension SIFT descriptor is computed.

Figure 10:
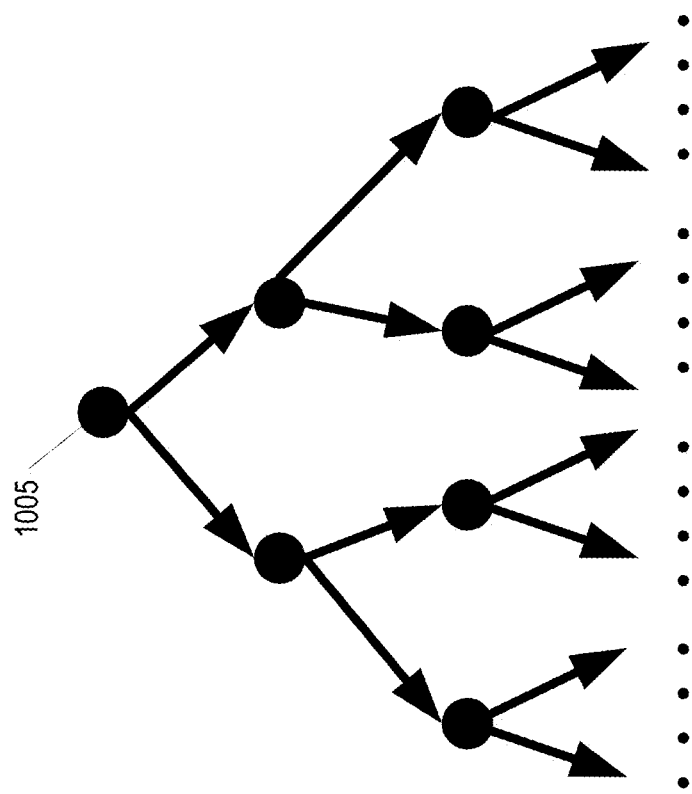
FIG. 10 shows a complete binary search tree structure which represents a vocabulary dictionary structure.

In some embodiments, a modified vocabulary tree structure is utilized to construct a visual vocabulary dictionary. The vocabulary tree defines a hierarchical quantization using a hierarchical k-means clustering. FIG. 10 shows a complete binary (k=2) search tree structure which represents a vocabulary dictionary structures. The node 1005 is a visual cluster center. $2^{nd}$ leaf nodes are finally used as visual vocabulary words. $n_d$ is the depth of the binary tree. In the vocabulary tree learning stage, first the initial k-means algorithm is applied on to the training data (a collection of SIFT descriptors derived from training data set) and then partitioned into 2 groups, where each group comprises SIFT descriptors closest to the cluster center. This process is then recursively applied until tree depth reaches $n_d$. In the online stage, a SIFT descriptor (a vector) is passed down the tree by each level via comparing this feature vector to the 2 cluster centers and choosing the closest one. The visual word histogram is computed for all the dense SIFT descriptors on each image.

Figure 11:
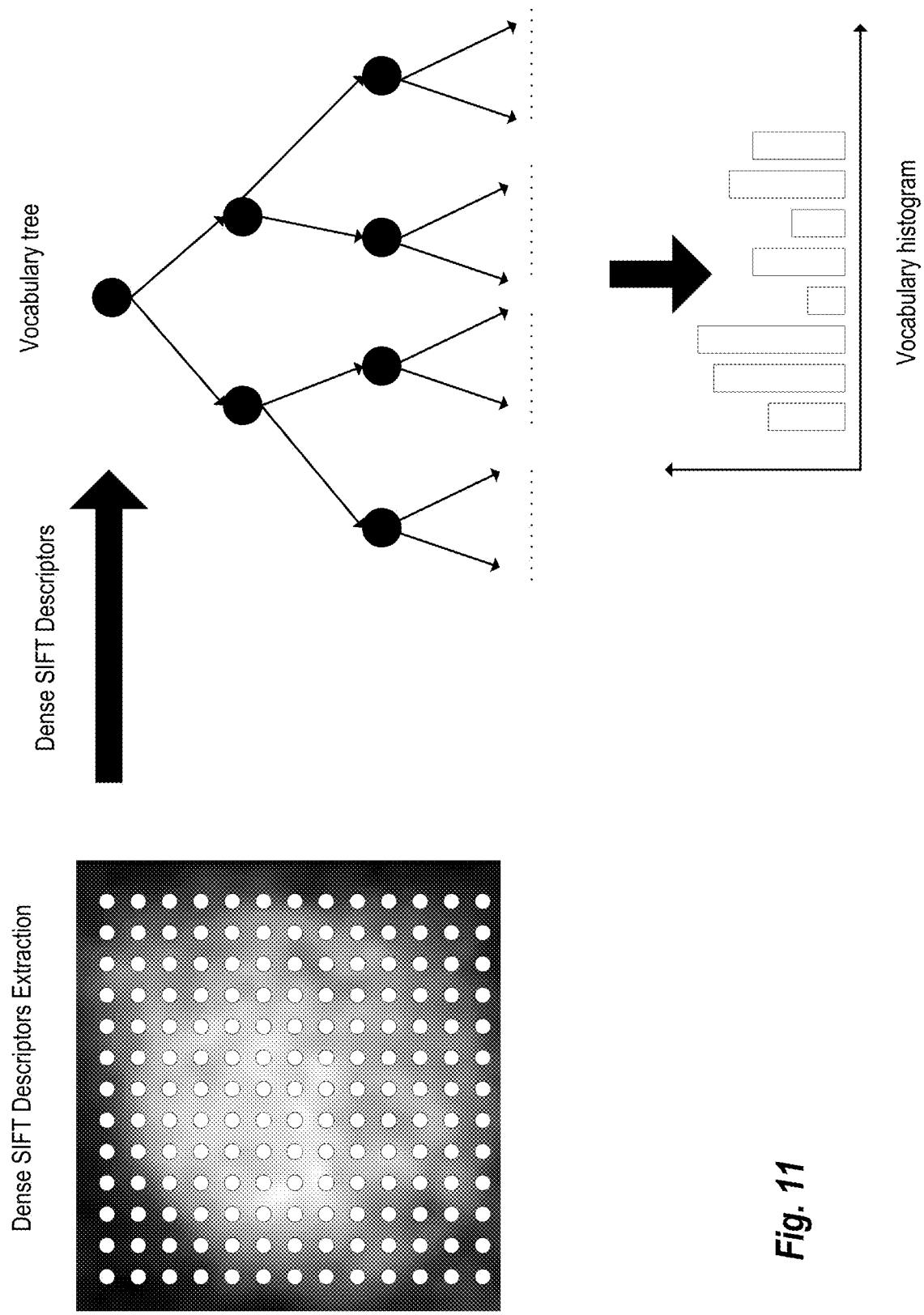
FIG. 11 provides a visualization of the workflow for the transformation from local image features (dense SIFT descriptor) to global image features (vocabulary histogram), as may be applied in some embodiments.

FIG. 11 provides a visualization of the workflow for the transformation from local image features (dense SIFT descriptor) to global image features (vocabulary histogram). The results obtained by combining SIFT features with SVM classification for an example dataset are depicted in FIG. 12. Combining these pairwise classifiers yielded an 84% correct classification rate for the 5-type classification problem.

In some embodiments, a Deep Learning (DL) architecture is used to perform the 5-type classification. While SVM is mainly formulated for binary classification, DL is inherently a multi-label classifier. To illustrate the DL classification technique, the convolutional network was directly trained for the multi-label classification problem. 500 cells were used for training, 100 for each category and the rest of the cells were used for testing.

Figure 13:
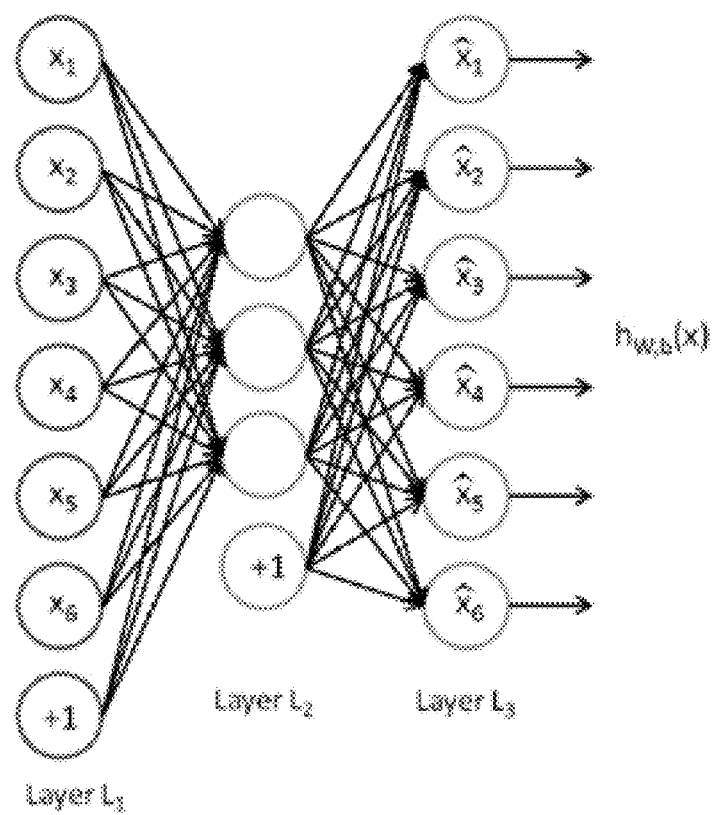
FIG. 13 shows the structure of a feed-forward neural network with one hidden layer that may be utilized in some embodiments.

For this example DL application, an auto-encoder convolutional neural network (CNN) was used to train the marginal space learning (MSL) classifier. FIG. 13 shows the structure of a feed-forward neural network with one hidden layer (also referred to as an "AE"). Ignoring the bias term (the nodes labeled as "+1" in FIG. 13), the input and output layers have the same number of nodes. The objective of such auto encoders is to learn a transfer function between the input layer (features that represent the images) and the output layer (the labels for the image). If the hidden layer has a size equal or larger than the input layer, potentially, an AE may learn an identity transformation. To prevent such a trivial solution, previously, an AE is set up with a hidden layer with fewer nodes than the input. Recently, denoising auto-encoder (DAE) was proposed to learn a more meaningful representation of the input. A certain percentage (e.g., 50%) of input nodes are randomly picked to be disturbed (e.g., set the value to zero) and the DAE is required to reconstruct the original input vector given a contaminated observation. With DAE, the hidden layer may have more nodes than the input to achieve an over-complete representation. After training an AE, the output layer is discarded and another AE is stacked using the activation response of the already trained hidden layer as input to the new AE. This process can be repeated to train and expand a network layer by layer. After pre-training, the output of the hidden layers can be treated as high-level image features to train a classifier. Alternatively, we can add one more layer for the target output and the whole network can be refined using back-propagation.

After the classification is done, the various categories of white blood cells may be presented to the pathologist in a graphical user interface (GUI) for final confirmation. The probability of a given cell belonging to a certain sub-type may be calculated and presented numerically or graphically to the pathologist during the final check.

Figure 14:
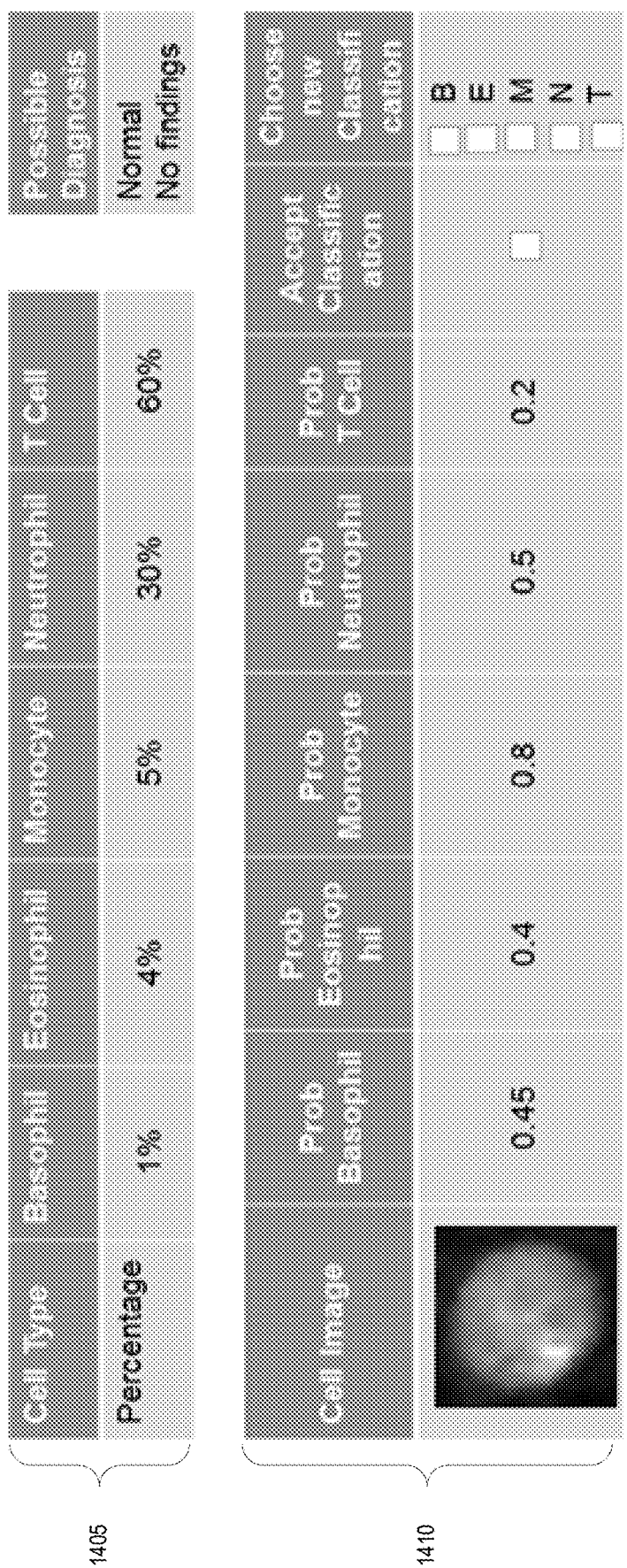
FIG. 14 shows a GUI which provides for results visualization and facilitates user interaction and correction, according to some embodiments.

FIG. 14 shows a GUI which provides for results visualization and facilitates user interaction and correction, according to some embodiments. As shown in the FIG. 14, the pathologist will have a chance to make a modification based on the DHM image of the cells. The results of the automatic blood differential is depicted at the top two rows 1405 displaying the percentage of each blood cell type and the possible diagnosis based on these percentages. The bottom part of the FIG. 1410 shows how the user can modify the results. The system shows the top cell candidates for user interactions. These cells are chosen and sorted based on the difference of the top two probabilities. The system displays the extracted cell (extracted by our preprocessing pipeline) and displays the probability of it belonging to each WBC type. The user can accept the label or choose a new label by simply marking a check box. If the user changes the label, the system may automatically update the counts, the percentages and the possible diagnosis, which changes the top row and displays the new results.

Additionally, in order for pathologist to best be able to review the images, in some embodiments, a pseudo-colorization scheme is utilized which converts the DHM images into an image with a color pattern similar to cell images stained for conventional staining methodologies such as the Wright and Giemsa methodologies. For example, Giemsa-Wright stains use solutions which include eosin Y, azure B, and methylene blue for staining. These solutions bind to the constituents of the cells including nucleus and granules differently and thereby provide a more pronounced coloring which is essential for visual inspection of the cells. From a DHM image of a cell, we obtain different optical density patterns for the cell constituents and that could be used as a feature to perform colorization. The method that we envision is based on having matched pairs of cells which are imaged both with DHM and Giemsa staining respectively. In some embodiments a simple regression function is used, which can be implemented using a machine learning technique such as a convolutional neural network to map optical density maps from DHM to the RGB color scheme consistent with Giemsa-Wright staining protocol. The regression map could work either on the single pixel or groups of pixels (i.e., image patches). In addition, a Markov random field based regularization may be utilized to make sure that the neighboring pixels with similar optical density will be colored similarly. Aside from Giemsa and Wright stains, other staining protocols can be learned based on set of matching pairs of cellular images and the stained version can be digitally reproduced from the DHM images.

In some embodiments, the mean cell volume computation for RBC described herein and/or the WBC five part differential may be used as key measurements for a Complete Blood Count (CBC) test. As is understood in the art, a CBC test evaluates an individual's overall health and may be used in the detection of blood-related disorders such as anemia, infection and leukemia. So, for example, abnormal increases or decreases in particular WBC counts may be used as an indicator of an underlying medical condition that calls for further evaluation.

Various other extensions, enhancements, or other modifications may be made or added to the techniques described herein to provide additional functionality. For example, in some embodiments, the five part differential methodology for white blood cell sub-typing is applied on raw fringe pattern images prior to the reconstruction as well. In order to increase the overall accuracy of either RBC volume or WBC classification, multiple images of the same cell could be used and the results could be averaged. The systems and methods described herein may also be applied to clinical applications outside the cell classification space. For example, the size calculation and classification of various objects based on the methodology described can be extended for urine analysis applications, where the size of urine sediments are measured and various kinds are identified by analyzing the DHM images using the methodology described. Additionally, given the latest advancements in DHM technology—particularly reductions in size, complexity and cost—these (and other) applications could be performed within a clinical environment or at the point of care (in a decentralized manner).

Figure 15:
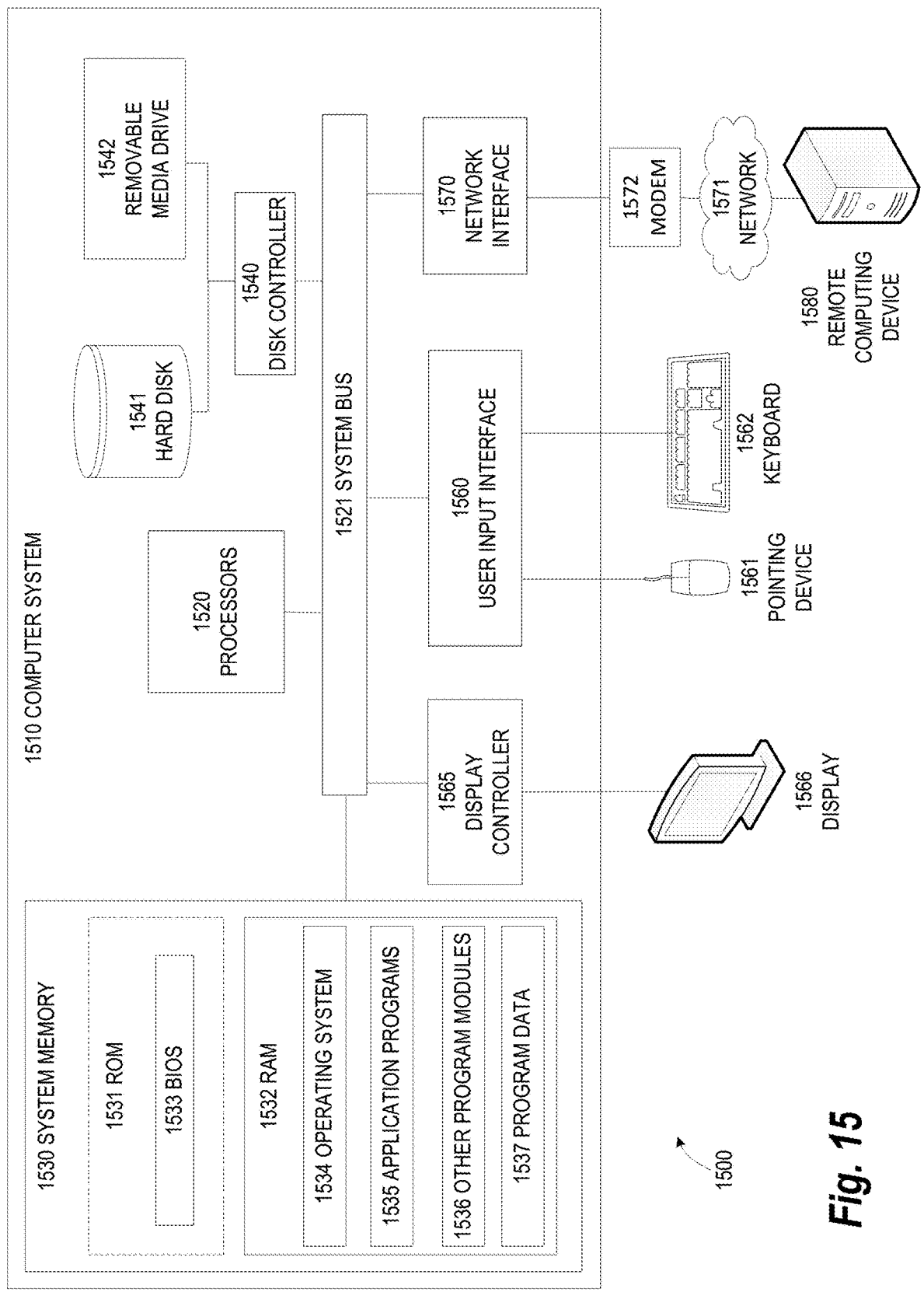
FIG. 15 illustrates an exemplary computing environment within which embodiments of the invention may be implemented

FIG. 15 illustrates an exemplary computing environment 1500 within which embodiments of the invention may be implemented. For example, this computing environment 1500 may be configured to execute one or more of the components of the framework 100 for processing DHM images illustrated in FIG. 1. Additionally (or alternatively), this computing environment 1500 may be configured to perform one or more of the processes described herein (e.g., the process 500 for calculating cell volume shown in FIG. 1. The computing environment 1500 may include computer system 1510, which is one example of a computing system upon which embodiments of the invention may be implemented. Computers and computing environments, such as computer system 1510 and computing environment 1500, are known to those of skill in the art and thus are described briefly here.

As shown in FIG. 15, the computer system 1510 may include a communication mechanism such as a bus 1521 or other communication mechanism for communicating information within the computer system 1510. The computer system 1510 further includes one or more processors 1520 coupled with the bus 1521 for processing the information. The processors 1520 may include one or more central processing units (CPUs), graphical processing units (GPUs), or any other processor known in the art.

The computer system 1510 also includes a system memory 1530 coupled to the bus 1521 for storing information and instructions to be executed by processors 1520. The system memory 1530 may include computer readable storage media in the form of volatile and/or nonvolatile memory, such as read only memory (ROM) 1531 and/or random access memory (RAM) 1532. The system memory RAM 1532 may include other dynamic storage device(s) (e.g., dynamic RAM, static RAM, and synchronous DRAM). The system memory ROM 1531 may include other static storage device(s) (e.g., programmable ROM, erasable PROM, and electrically erasable PROM). In addition, the system memory 1530 may be used for storing temporary variables or other intermediate information during the execution of instructions by the processors 1520. A basic input/output system (BIOS) 1533 containing the basic routines that help to transfer information between elements within computer system 1510, such as during start-up, may be stored in ROM 1531. RAM 1532 may contain data and/or program modules that are immediately accessible to and/or presently being operated on by the processors 1520. System memory 1530 may additionally include, for example, operating system 1534, application programs 1535, other program modules 1536 and program data 1537.

The computer system 1510 also includes a disk controller 1540 coupled to the bus 1521 to control one or more storage devices for storing information and instructions, such as a hard disk 1541 and a removable media drive 1542 (e.g., floppy disk drive, compact disc drive, tape drive, and/or solid state drive). The storage devices may be added to the computer system 1510 using an appropriate device interface (e.g., a small computer system interface (SCSI), integrated device electronics (IDE), Universal Serial Bus (USB), or FireWire).

The computer system 1510 may also include a display controller 1565 coupled to the bus 1521 to control a display 1566, such as a cathode ray tube (CRT) or liquid crystal display (LCD), for displaying information to a computer user. The computer system includes an input interface 1560 and one or more input devices, such as a keyboard 1562 and a pointing device 1561, for interacting with a computer user and providing information to the processor 1520. The pointing device 1561, for example, may be a mouse, a trackball, or a pointing stick for communicating direction information and command selections to the processor 1520 and for controlling cursor movement on the display 1566. The display 1566 may provide a touch screen interface which allows input to supplement or replace the communication of direction information and command selections by the pointing device 1561.

The computer system 1510 may perform a portion or all of the processing steps of embodiments of the invention in response to the processors 1520 executing one or more sequences of one or more instructions contained in a memory, such as the system memory 1530. Such instructions may be read into the system memory 1530 from another computer readable medium, such as a hard disk 1541 or a removable media drive 1542. The hard disk 1541 may contain one or more datastores and data files used by embodiments of the present invention. Datastore contents and data files may be encrypted to improve security. The processors 1520 may also be employed in a multi-processing arrangement to execute the one or more sequences of instructions contained in system memory 1530. In alternative embodiments, hard-wired circuitry may be used in place of or in combination with software instructions. Thus, embodiments are not limited to any specific combination of hardware circuitry and software.

As stated above, the computer system 1510 may include at least one computer readable medium or memory for holding instructions programmed according to embodiments of the invention and for containing data structures, tables, records, or other data described herein. The term "computer readable medium" as used herein refers to any medium that participates in providing instructions to the processor 1520 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 1541 or removable media drive 1542. Non-limiting examples of volatile media include dynamic memory, such as system memory 1530. Non-limiting examples of transmission media include coaxial cables, copper wire, and fiber optics, including the wires that make up the bus 1521. Transmission media may also take the form of acoustic or light waves, such as those generated during radio wave and infrared data communications.

The computing environment 1500 may further include the computer system 1510 operating in a networked environment using logical connections to one or more remote computers, such as remote computer 1580. Remote computer 1580 may be a personal computer (laptop or desktop), a mobile device, a server, a router, a network PC, a peer device or other common network node, and typically includes many or all of the elements described above relative to computer system 1510. When used in a networking environment, computer system 1510 may include modem 1572 for establishing communications over a network 1571, such as the Internet. Modem 1572 may be connected to bus 1521 via user network interface 1570, or via another appropriate mechanism.

Network 1571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 1510 and other computers (e.g., remote computer 1580). The network 1571 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 1571.

As one application of the exemplary computing environment 1500 to the technology described herein, consider an example system for analyzing DHM data for hematology applications which includes a network component, a modeling processor, and a GUI. The networking component may include network interface 1570 or some combination of hardware and software offering similar functionality. The networking component is configured to communicate with a DHM system to retrieve DHM images. Thus, in some embodiments, the networking component may include a specialized interface for communicating with DHM systems. The modeling processor is included in a computing system (e.g. computer system 1510) and is configured with instructions that enable it to train a classifier for cell types present in cell images extracted from DHM images received via the networking component. The modeling processor may include additional functionality, as described in this disclosure, to support this task (e.g., segmentation, identifying connected components, etc.). The modeling processor is further configured to use the classifier to determine the probability that new cell images belong to one of the types used to train the classifier. The GUI may then be presented on a display (e.g., display 1566) for review by a user.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

The invention claimed is:

1. A method for analyzing digital holographic microscopy (DHM) data for hematology applications to perform white blood cell differentiation, the method comprising:
   receiving a plurality of DHM images acquired using a digital holographic microscopy system;
   identifying one or more connected components in each of the plurality of DHM images;
   calculating a component size for each connected component;
   removing one or more disqualified connected components from the one or more connected components, wherein each disqualified connected component has a size below a first predetermined threshold value or above a second predetermined threshold value;
   generating one or more training white blood cell images from one or more remaining connected components having a size between the first predetermined threshold value and the second predetermined threshold value;
   training a classifier to identify a plurality of white blood cell types using the one or more training white blood cell images as an input to the classifier;
   extracting a new white blood cell image from a new DHM image;
   applying the classifier to the new white blood cell image to determine a plurality of probability values, each respective probability value corresponding to one of the plurality of white blood cell types; and
   presenting the new white blood cell image and the plurality of probability values in a graphical user interface.

2. The method of claim 1, further comprising:
   prior to identifying the one or more connected components, applying a thresholding to the each of the plurality of DHM images to highlight bright spots in each respective DHM image.

3. The method of claim 1, wherein the classifier is a K-Nearest Neighbor (K-NN) classifier.

4. The method of claim 3, wherein the classifier uses texton-based texture features extracted from each of the plurality of DHM images to classify the new DHM image.

5. The method of claim 1, wherein the classifier is a deep learning classifier trained using an auto-encoder convolutional neural network (CNN).

6. The method of claim 5, the CNN includes an input layer, a hidden layer and an output layer, wherein the input layer and the output layer have the same number of nodes, and the hidden layer has fewer nodes than the input layer.

7. The method of claim 1, wherein the plurality of white blood cell types include a monocyte, a basophil, a neutrophil, an eosinophil and a lymphocyte.

8. The method of claim 1, further comprising:
converting the new white blood cell image into an image with a color pattern through a pseudo-colorization scheme.

9. The method of claim 1, further comprising:
determining a mapping between optical density and coloring associated with a Giemsa-Wright staining protocol; and
determining optical density information associated with the new white blood cell image; and
prior to presenting the new white blood cell image, colorizing the new white blood cell image using the mapping and the optical density information.

10. The method of claim 9, wherein the step of colorizing the new white blood cell image further comprising:
colorizing neighboring pixels of the new white blood cell image with similar optical density similarly through Markov random field based regularization.

11. The method of claim 1, further comprising:
performing a complete blood cell (CBC) test using the plurality of probability values.

12. An article of manufacture for analyzing digital holographic microscopy (DHM) data for hematology applications to perform white blood cell differentiation, the article of manufacture comprising a non-transitory, tangible computer-readable medium holding computer-executable instructions for performing a method comprising:
receiving a plurality of DHM images acquired using a digital holographic microscopy system;
identifying one or more connected components in each of the plurality of DHM images;
calculating a component size for each connected component;
removing one or more disqualified connected components from the one or more connected components, wherein each disqualified connected component has a size below a first predetermined threshold value or above a second predetermined threshold value;
generating one or more training white blood cell images from one or more remaining connected components having a size between the first predetermined threshold value and the second predetermined threshold value;
training a classifier to identify a plurality of white blood cell types using the one or more training white blood cell images as an input to the classifier;
extracting a new white blood cell image from a new DHM image;
applying the classifier to the new white blood cell image to determine a plurality of probability values, each respective probability value corresponding to one of the plurality of white blood cell types; and
presenting the new white blood cell image and the plurality of probability values in a graphical user interface.

13. The article of manufacture of claim 12, wherein the method further comprises:
prior to identifying the one or more connected components, applying a thresholding to the plurality of DHM images to highlight bright spots in each respective DHM image.

14. The article of manufacture of claim 12, wherein the classifier uses texton-based texture features extracted from each of the plurality of DHM images to classify the new DHM image.

15. The article of manufacture of claim 12, wherein the classifier is a visual vocabulary dictionary trained using hierarchical k-means and a scale-invariant feature transform (SIFT) descriptor as a local image feature.

16. The article of manufacture of claim 12, wherein the classifier is a marginal space learning (MSL) classifier trained using an auto-encoder convolutional neural network (CNN).

17. The article of manufacture of claim 12, wherein the method further comprises:
determining a mapping between optical density and coloring associated with a Giemsa-Wright staining protocol; and
determining optical density information associated with the new white blood cell image; and
prior to presenting the new white blood cell image, colorizing the new white blood cell image using the mapping and the optical density information.

18. A system for analyzing digital holographic microscopy (DHM) data for hematology applications to perform white blood cell differentiation, the system comprising:
a network interface configured to communicate with a digital holographic microscopy system to retrieve a plurality of training DHM images and a test DHM image;
a modeling processor configured to:
identify one or more connected components in each of the plurality of training DHM images,
calculate a component size for each connected component,
remove one or more disqualified connected components from the one or more connected components, wherein each disqualified connected component has a size below a first predetermined threshold value or above a second predetermined threshold value,
generate one or more training white blood cell images from one or more remaining connected components having a size between the first predetermined threshold value and the second predetermined threshold value,
train a classifier to identify a plurality of white blood cell types using the one or more training white blood cell images as an input to the classifier,
extract a test white blood cell image from the test DHM image, and
apply the classifier to the test white blood cell image to determine a plurality of probability values, each respective probability value corresponding to one of the plurality of white blood cell types; and
a graphical user interface configured to present the test white blood cell image and the plurality of probability values.

* * * * *